United States Patent [19]

Turner et al.

[11] Patent Number: 5,017,378
[45] Date of Patent: May 21, 1991

[54] INTRAORGAN INJECTION OF BIOLOGICALLY ACTIVE COMPOUNDS CONTAINED IN SLOW-RELEASE MICROCAPSULES OR MICROSPHERES

[75] Inventors: Terry L. Turner; Stuart S. Howards, both of Charlottesville, Va.

[73] Assignee: The University of Virginia Alumni Patents Foundation, Charlottesville, Va.

[21] Appl. No.: 345,226

[22] Filed: May 1, 1989

[51] Int. Cl.$^5$ ............................................. A61F 2/00
[52] U.S. Cl. ................................. 424/422; 424/423; 424/426
[58] Field of Search ....................... 424/422, 423, 426; 530/399

[56] References Cited

U.S. PATENT DOCUMENTS

| | | | |
|---|---|---|---|
| 4,150,108 | 4/1979 | Graham | 424/423 |
| 4,349,530 | 9/1982 | Royer | 424/426 |
| 4,357,934 | 11/1982 | Fahim | 514/179 X |
| 4,389,330 | 6/1983 | Tice et al. | 424/426 |
| 4,391,909 | 7/1983 | Lim | 424/426 |
| 4,419,340 | 12/1983 | Yolles | 424/422 |
| 4,558,690 | 12/1985 | Joyce | 424/422 |
| 4,732,763 | 3/1988 | Beck et al. | 424/426 |

OTHER PUBLICATIONS

Lewis et al., "Overview of Controlled Release Systems of Male Contraception", *Male Contraception: Advances and Future Prospects*, Harper & Rowe, pp. 336–346 (U.S.A. 1986).

Asch et al., "Preliminary Results on the Effects of Testosterone Microcapsules", *Male Contraception: Advances and Future Prospects*, Harper & Rowe, pp. 347–360 (U.S.A. 1986).

Beck et al., "New Long-Acting Injectable Microcapsule Contraceptive System", J. Obstet. Gyn., 135:419–426 (U.S.A. 1979).

Beck et al., "Clinical Evaluation of Injectable Biodegradable Contraceptive System", Am. J. Obstet, Gynec., 140:799–806 (U.S.A. 1981).

Beck et al., "Clinical Evaluation of an Improved Injectable Microcapsule Contraceptive System", Am. J. Obstet. Gynec., 147:815–821 (U.S.A. 1983).

Rivera et al., "Norethisterone Microspheres 6-Month System: Clinical Results", *Long-Acting Contraceptive Delivery Systems*, Harper & Rowe (U.S.A. 1984).

Primary Examiner—Thurman K. Page
Assistant Examiner—J. Spear
Attorney, Agent, or Firm—James C. Wray

[57] ABSTRACT

A method for increasing fertility in males with impairment of testosterone synthesis, comprising the step of injecting slow-release microcapsules or microspheres containing testosterone directly into the testes. The testosterone-laden microcapsules or microspheres act as temporary Leydig cells and release testosterone directly into the testicular parenchyma and maintain high intratesticular concentrations of testosterone needed for spermatogenesis.

1 Claim, 2 Drawing Sheets

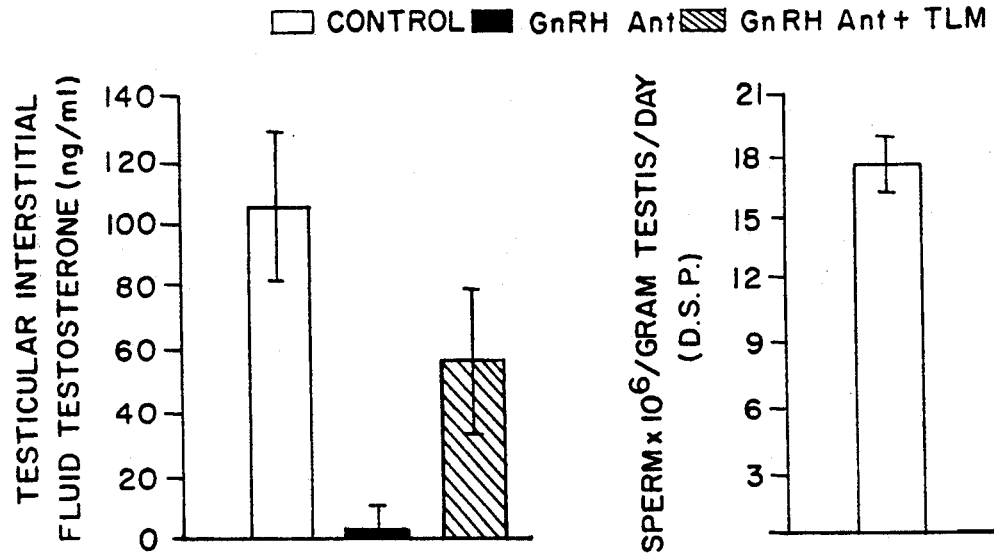
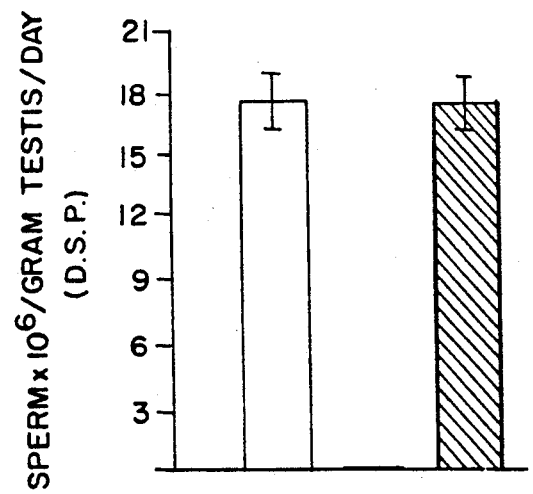
FIG. 3A
FIG. 3B
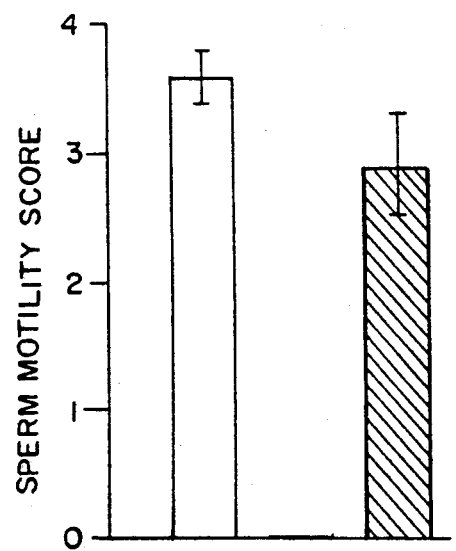
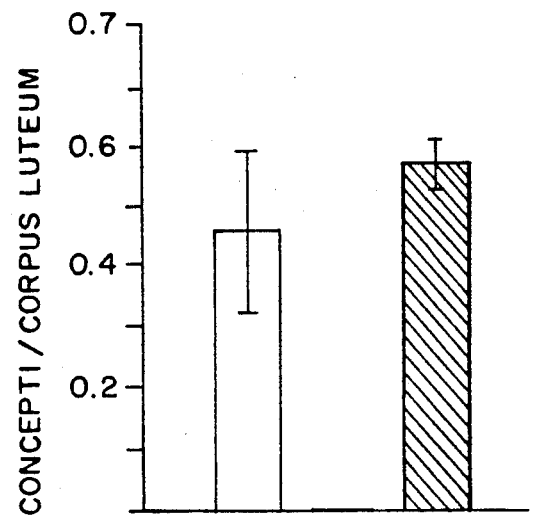
FIG. 3C
FIG. 3D

INTRAORGAN INJECTION OF BIOLOGICALLY ACTIVE COMPOUNDS CONTAINED IN SLOW-RELEASE MICROCAPSULES OR MICROSPHERES

BACKGROUND OF THE INVENTION

1. Field of the Invention

This invention relates to a novel method for increasing fertility in males with impairment of testosterone synthesis by injecting slow-release microcapsules or microspheres containing testosterone directly into infertile testes to stimulate Leydig cells. 2. Prior Art Approximately 5 percent of American couples are infertile due to male infertility alone (approximately 2.5 million men), and 75 percent of these males have pathologies associated with low testosterone output by the testes (approximately 1.9 million men). Direct testicular injection of slow-release testosterone encapsulations could be efficacious in increasing the fertility of many of these men.

No thought has apparently been given to the method of using testosterone-laden microspheres for fertility enhancement rather than fertility reduction. Testosterone is required for spermatogenesis. Normally, the Leydig cells of the testes secrete testosterone directly into the testicle interstitial fluid and maintain the locally high testosterone concentration required for the maintenance of robust spermatogenesis. In some males, this fails to occur. Leydig cells either fail to produce testosterone at all, or fail to secrete it in sufficient amounts to maintain normal spermatogenesis.

Microcapsulation of bioactive compounds (primarily steroid hormones) has been performed for almost ten years. The microcapsulation process itself is covered by U.S. Pat. No. 4,489,330.

Beck et al first reported the use of biodegradable microspheres for the encapsulation of a steroid hormone and the intramuscular injection of those microspheres as a long-acting method for the slow-release of norethisterone into the bloodstream (Beck et al., "New Long-Lasting Injectable Microcapsule Contraceptive System", J. OBSTET. GYN., 135:419–426 (1979)). The concept was to provide a method of long-term steroid delivery for women for purposes of contraception. This work has been followed up by studies which examine the efficiency of this contraceptive delivered to human females (Beck et al., "Clinical Evaluation of Injectable Biodegradable Contraceptive System", AM. J. OBSTET. GYNEC., 140:799–806 (1981); Beck et al., "Clinical Evaluation of and Improved Injectable Microcapsule Contraceptive System", AM. J. OBSTET. GYNEC, 147:815–821 (1983); Rivera et al., "Norethisterone Microspheres Six-Month System: Clinical Results", *Long-Acting Contraceptive Delivery Systems*, Harper and Row (1984)). Since at least 1980 there has been work on the encapsulation of other hormones in biodegradable microspheres, and in 1986 a method was disclosed for the manufacture of testosterone—containing biodegradable microspheres (Lewis et al., "Overview of Controlled Release Systems of Male Contraception" and Asch et al., "Preliminary Results on the of Testosterone Microcapsules", *Male Contraception: Advances and Future Prospects*, Harper and Row (1986)). These were developed with the thought of using such microspheres in applications towards male contraception or virilizing males with hypopituitary or hypogonadal function.

SUMMARY OF THE INVENTION

The present invention injects directly into the testes small volumes of testosterone-laden microspheres or microcapsules which can act as temporary Leydig cells. These microspheres or microcapsules can release the testosterone directly into the testicular parenchyma which would bypass the need to regulate pituitary function or peripheral testosterone concentrations and maintain the high intratesticular concentrations of testosterone needed for spermatogenesis. Under this method, a small percutaneous injection of slow-release microspheres would maintain high intratesticular testosterone concentration for a long enough period of time to allow more than one spermatogenic cycle.

This treatment has the advantage of simplicity, requires no surgery, can be performed on an outpatient basis, requires no follow-up action by the patient, is self-reversing, and can be used multiple times in the same patient.

These and other and further objects and features of the invention are apparent in the disclosure, which includes the above and ongoing specification with the claims.

BRIEF DESCRIPTION OF THE DRAWINGS

FIGS. 3 A–D are grafts of the effect of 90-day treatment of adult male rats with GnRH antagonist or GnRH antagonist +20 mg testosterone-laden microspheres injected directly into the testis (TLM). Specifically:

FIG. 3A is a graph showing testicular interstitial fluid testosterone concentrations;

FIG. 3B is a graph showing daily sperm production/testis;

FIG. 3C is a graph showing sperm motility score;

FIG. 3D is a graph showing concepti/corpus luteum.

DETAILED DESCRIPTION OF THE INVENTION

Experiments were conducted on rats to demonstrate that the method of injecting testosterone-laden microspheres into the testes is workable.

EXPERIMENT I

Titration of Microsphere Dose to Rat Testis

Testosterone-laden, biodegradable, polylactone microspheres (TLM) incorporating 50% testosterone (w/w) (Stoelle Research & Development, Lebanon, Ohio) were used in these experiments. This microsphere formulation has been shown to release testosterone for 90 days after a single intramuscular injection. No previous work had been done with testicular injection and so it was not known whether the different fluid dynamics in the testis would alter the steroid release rate or duration of release from these microspheres. Crude calculations based on data from primate studies using intramuscular injection of hormone containing microspheres, data from our lab concerning normal intratesticular testosterone concentrations and daily testosterone release by the normal rat testis, and the knowledge of the testosterone/ polylactone ratio in the microspheres, allowed us to estimate that each rat testis would require a dose of between 2.0 mg to 20.0 mg TLM in order to maintain normal intratesticular testosterone concentrations.

This experiment was performed with four control animals and two animals each receiving 0.5 mg estradiol/day, subcutaneously, in 0.1 ml corn oil plus 0, 1, 2, 10 or 20 mg TLM. TLM were suspended in 40 ul 10% ethanol in saline immediately prior to intratesticular injection. Control animals received corn oil subcutaneously and vehicle intratesticularly. Both testes of one animal each received either 1, 2, 10, or 20 mg testosterone in the slow-release microspheres. The TLM injection was performed with a 100 μl glass syringe and a 20 gauge needle. Mineral oil was first drawn into the needle to fill the needle barrel and hub to the bottom of the syringe plunger. Forty μl of stirred TLM solution was drawn into the syringe. The testes of anesthetized rats were exposed through a mid-ventral laparotomy and TLM were injected under the tunica albuginea into the testicular intratubular space in the lower third of each testis of each animal. The needle was withdrawn with little TLM loss through the tunica, and the testis was returned to the scrotum. The animal was recovered and 5 days allowed to pass to allow equilibration of testosterone release. All animals injected with the testosterone-laden microspheres, plus one additional uninjected animal, began receiving either corn oil or 500 ng estradiol/day in corn oil by subcutaneous injection. After 15 days, testes were obtained and weighed and the serum and testicular interstitial fluid (TIF) were obtained for testosterone analysis by RIA. Similar values were obtained from two control animals.

Figure 1:
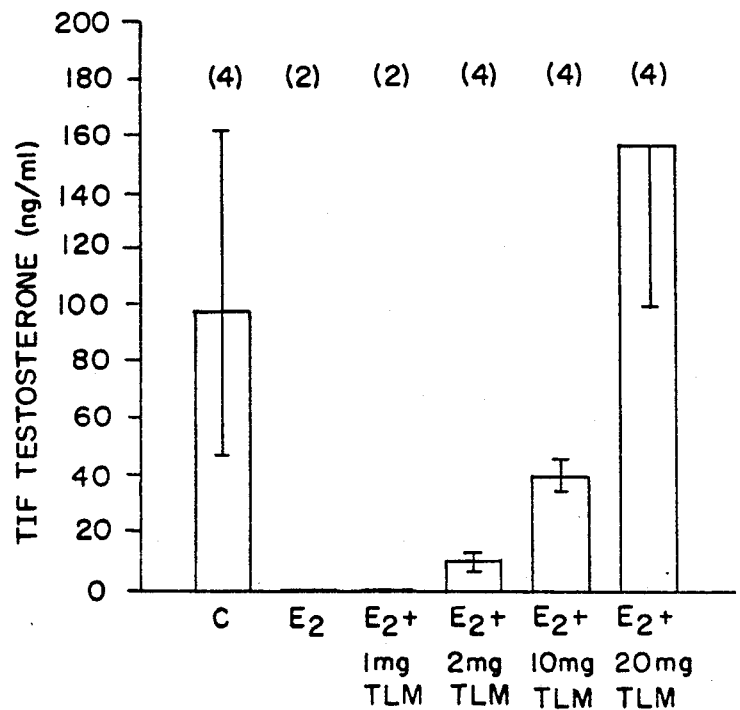
FIG. 1 is a graph showing the testicular interstitial fluid (TIF) testosterone concentrations in rats after 15 days of treatment. C, control (corn oil injections s.c., vehicle only injections intratesticularly); $E_2$, estradiol alone (estradiol in corn oil, s.c.); $E_2+1.0$ mg TLM, estradiol in corn oil s.c. plus 1 mg TLM injected intratesticularly through a laparotomy incision; $E_2+2$ mg same as before, but injected dose of TLM was 2 mg; $E_2+10$ mg TLM, same as before, but injected dose of TLM was 10 mg; $E_2+20$ mg TLM, same as before, but injected dose of TLM was 20 mg.

TIF testosterone concentrations in control animals were approximately 100 ng/ml. These values are consistent with literature values, and were completely replaced in testes receiving single injections of 20 mg testosterone in microspheres. Estradiol treatment resulted in TIF testosterone concentrations being below detectable limits and this was not altered by the 1 mg TLM/testis dose (FIG. 1). Doses of 2 mg, 10 mg, and 20 mg TLM/testis raised TIF testosterone concentrations in a dose-response manner. Serum testosterone concentrations were approximately 1.0 ng/ml in control animals, a value consistent with literature values. The serum testosterone concentrations in the animal receiving 20 mg testosterone/testis were normal. Testis weights were approximately 2.0 g/testis in control animals, reduced by half by the estradiol treatment, and not appreciably altered from that by the androgen replacement therapy in this first trial.

EXPERIMENT II

Injection of 20 mg Testosterone/Testis by Mid-ventral Laparotomy (MVL) and Percutaneous Injection (PCI)

This experiment had four groups: control (n=4), estradiol treatment (n=2), TLM administered by direct visualization through mid-ventral laparotomy (MVL; n=9), and TLM administered by nonsurgical, percutaneous injection of TLM (PCI; n=4). PCI administration of TLM was performed on anesthetized adult rats. The TLM solution (20 mg TLM/40 μl 10% ethanol:saline) was prepared in a syringe as previously described. The tip of the 20 gauge needle was positioned in the lower third of the testis, as best as could be estimated externally, with the injection site being near the distal pole of the testis. The injection site was off center of the bottom of each hemi-scrotum in order to avoid the testicular artery which circumnavigates the pole at a central longitude.

Figure 2:
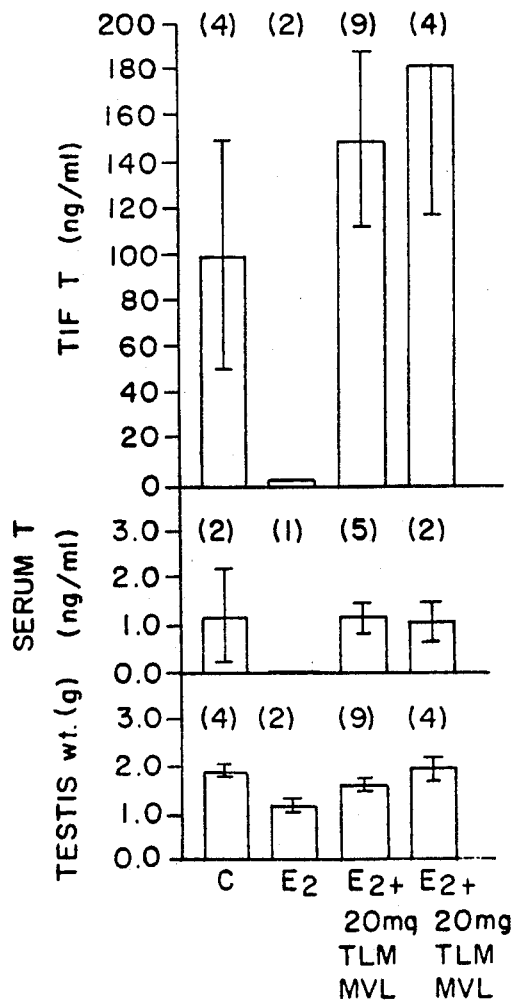
FIG. 2 is a graft showing the testicular interstitial fluid (TIF) and serum testosterone concentrations and testis weights in rats after 15 days of treatment. C, control (corn oil injections s.c., vehicle only injections intratesticularly); $E_2$, estradiol alone (estradiol in corn oil s.c.); $E_2+20$ mg TLM MVL (estradiol in corn oil s.c. +20 mg testosterone-laden microspheres (TLM) injected intratesticularly through a mid-ventral laparotomy (MVL); $E_2+20$ mg TLM PCI (estradiol in corn oil s.c. +20 mg TLM delivered by direct, nonsurgical, percutaneous intratesticular injection (PCI).

As above, the animals began receiving estradiol 5 days after receiving their microsphere injection, and the experiment was terminated 15 days later. The data from control animals and those receiving estradiol alone in the previous experiment were used for comparison. Fifteen-day estradiol treatment reduced TIF and peripheral serum testosterone concentrations to below detectable limits (FIG. 2) and caused a significant reduction (p <0.05) in testis weights as well (FIG. 2). Testes receiving daily estradiol plus testosterone microspheres by MVL had normal intratesticular testosterone concentrations, serum testosterone concentrations, qualitative epididymal appearance, testis weights significantly higher than those with estradiol alone, and normal cauda sperm motility. Testicles receiving microspheres by direct PCI had normal TIF testosterone concentrations, testis weights, cauda sperm motility, and serum testosterone concentrations, along with a normal qualitative appearance of the epididymides.

EXPERIMENT III

20 mg TLM Administration by Direct Intra-testicular Injection in Hypogonadotropic Rats Adult, male, Sprague-Dawley rats (450–550 g) were used. Osmotic minipumps (model 2001, Alza Corp., Palo Alto, Calif.) with a constant secretion of 12 μl/day for 17 days were pre-loaded with either Boyd's buffer alone or Boyd's buffer +GnRH-A at a concentration of 21 μg/μl to achieve a total dose of 25 μg GnRH-A/day/animal. The experimental period was 90 days. All animals received intraperitoneal minipumps on day 0 and replacement pumps on days 15, 30, 45, 60, and 75.

Control animals received minipumps containing Boyd's buffer alone and a single intratesticular injection of 40 μl vehicle alone. The GnRH-A group received minipumps containing Boyd's buffer +GnRH-A and the TLM group received minipumps containing GnRH-A +20 mg TLM/testis. TLM were delivered intratesticularly by percutaneous injection as described previously. Different groups of control and treatment animals were terminated on day 45 and day 90 after initiation of the study. Cardiac blood serum and TIF were obtained and analyzed for testosterone as described above. Animal weights (g), testicular weights (g), daily sperm production (sperm/g of testis/day)[9] and cauda sperm motility score (0–4)[10] were determined on all animals. Fertility rates were also determined for animals in the 90-day groups. Fertility trials consisted of placing one male with three females for 8 days prior to the termination date, then removing the male on that date. The females were sacrificed 10 days later and examined to determine the number of females impregnated/male, the number of concepti/females, and the number of concepti/corpus luteum. Data were similar for the 45-day groups and the 90-day groups, so only the 90 day data will be presented (FIG. 3).

Average body weights in the various groups averaged from 480–520 g, but no groups were significantly different from any other group (data not shown).

Average testis weights in GnRH-A treated animals (0.3±0.01 g) were significantly less than controls (1.90±0.04 g) and TLM treatment returned testis weights toward normal (1.20±0.02 g). Epididymal weights followed a similar pattern (control, 0.70±0.04 g; GnRH-A, 0.10±0.01 g; TLM, 0.50±0.01 g).

TIF testosterone concentrations in control animals (105±25 ng/ml) were significantly reduced by GnRH-A to 3±2 ng/ml (FIG. 3A). GnRH-A+TLM treatment significantly increased ($p<0.05$)-TIF TIF testosterone concentrations to 54±24 ng/ml (FIG. 3A).

GnRH-A treatment for 90 days significantly reduced daily sperm production (FIG. 3B), cauda sperm motility scores (FIG. 3C), and fertility as expressed by concepti per corpus luteum (FIG. 3D) to 0 GnRH-A +TLM returned all three parameters to values not significantly different (p 0.05) from controls (FIGS. 3B, C, D). Fertility rates were similar between control and GnRH-A +TLM whether expressed as concepti/corpus luteum (FIG. 3D) or females impregnated/male or concepti/female (data not shown).

GnRH-A treatment of male rats for 90 days effectively inhibited gonadotropin secretion which halted testosterone production, and eliminated sperm production and fertility. A single injection of 20 mg TLM maintained intratesticular testosterone concentrations at a level sufficient to maintain normal spermatogenesis and male fertility. Further preliminary data (not shown) indicate that 90 days is near the end of the effective life of the present TLM formulation with regard to testosterone release. This is consistent with information from the manufacturer.

These experiments demonstrate that the method of injecting testosterone-laden microspheres into the testis is workable in rats with regard to (1) maintaining normal intratesticular testosterone concentrations in the absence of testosterone secretion by Leydig cells, (2) maintains normal testis weights, (3) maintains normal serum testosterone concentrations, (4) maintains normal cauda sperm motility, and (5) maintains normal sperm output so far as it can be judged qualitatively by the apparent filling of the epididymal tubules. Furthermore, the microspheres can be delivered by direct percutaneous injection, a procedure that can be done on a low cost, outpatient basis.

While the invention has been described with reference to specific embodiments, modification and variations of the invention may be made without departing from the scope of the invention which is defined in the following claims.

We claim:

1. A method for increasing fertility in males with impairment of testosterone synthesis, comprising the step of:

injecting slow-release microcapsules or microspheres containing testosterone directly into testes, wherein the microcapsules or microspheres containing testosterone act as temporary Leydig cells and release testosterone directly into a testicular parenchyma and maintain intratesticular concentration of testosterone sufficient for spermatogenesis, wherein the slow-release microcapsules or microspheres are slow-release biodegradable polyactone microcapsules or microspheres.

* * * * *